United States Patent [19]

Shanzer et al.

[11] Patent Number: 4,590,005
[45] Date of Patent: May 20, 1986

[54] SOME MACROCYCLIC COMPOUNDS AND THEIR PREPARATION

[76] Inventors: Abraham Shanzer, 1 Hagedud Haivri Street, Bat Yam; Eduard Schwartz, Histadrut 1074/2, Ashdod, both of Israel

[21] Appl. No.: 726,946

[22] Filed: Apr. 26, 1985

Related U.S. Application Data

[63] Continuation of Ser. No. 262,508, May 11, 1981, abandoned, which is a continuation-in-part of Ser. No. 178,905, Aug. 18, 1980, abandoned.

[30] Foreign Application Priority Data

Aug. 22, 1979 [IL] Israel ............................... 58084

[51] Int. Cl.$^4$ ................ C07D 257/02; C07D 323/00; C07D 341/00
[52] U.S. Cl. ............................... 260/239.3 R; 549/11; 549/263; 330/299
[58] Field of Search ................ 260/239.3 R; 549/11, 549/267

[56] References Cited

U.S. PATENT DOCUMENTS 3,987,061 10/1976 Pedersen ................ 260/340.2
4,165,321 8/1979 Harris et al. ................ 260/340.2
4,251,448 2/1981 Bauer et al. ................ 260/340.2

FOREIGN PATENT DOCUMENTS 3216084 11/1983 Fed. Rep. of Germany ........ 549/11

OTHER PUBLICATIONS

Shanzer et al., "Tetrahedron Letters" (1979) pp. 5019–5020.
Shanzer et al., "J. Chem. Soc., Chem. Communications" (1980) pp. 176–177.
Shanzer et al., "J.C.S. Chem. Comm." (1980) pp. 259–260.
Shanzer et al., "J.C.S. Chem. Comm." (1981) pp. 634–635.
Shanzer et al., "Angewandte Chemie", vol. 19, No. 4, Apr. 1980, pp. 326–327.
Shanzer et al., "J. Am. Chem. Soc.", vol. 81, pp. 7339–7340 (1981).
Shanzer et al., "Synthesis with Tin Templates: The Preparation of Macrocyclic Tetralactones" (no date).
Shanzer et al., "Catalytic Preparation of Macrocyclic", 'Crown Lactones' (no date).

*Primary Examiner*—Robert T. Bond
*Attorney, Agent, or Firm*—Browdy and Neimark

[57] ABSTRACT

The present invention relates to novel macrocyclic carbonyl compounds of the macrocyclic carbamate and lactone type, to chiral macrocyclic structures, to macrocyclic urea compounds and to macrocyclic thiolactones and to a process for the preparation of same. The process of the invention comprises reacting a stannoxane, silazane or silathiane compound with an activated carbonyl compound in an organic solvent at moderate temperature.

6 Claims, No Drawings

SOME MACROCYCLIC COMPOUNDS AND THEIR PREPARATION

RELATION TO OTHER APPLICATION

This application is a continuation, of application Ser. No. 262,508, filed May 11, 1981 now abandoned, which is a continuation-in-part application to U.S. patent application Ser. No. 178,905 filed on July 18, 1980, now abandoned, the contents of which are incorporated by reference.

FIELD OF THE INVENTION

The present invention relates to certain novel macrocyclic compounds and to a novel process for the production of both novel and known macrocyclic compounds. The novel process enables the preparation of macrocyclic carbonyl compounds of predetermined varying ring size and functionality by convenient routes.

According to a preferred embodiment of the invention cyclic stannoxanes are prepared from diols and dibutyl tin oxide or from diols and dibutyl tin diethoxide, and such stannoxanes are reacted with an activated carbonyl derivative to yield macrocyclic carbamates or lactones. Amongst suitable activated carbonyl derivatives there may be mentioned diisocyanates, diacyl chlorides, anhydrides or $\beta$-lactones. According to a further embodiment of the invention, cyclic stannoxanes are condensed with optically active acidic amino acid derivatives resulting in chiral macrocyclic structures. According to yet a further embodiment of the invention cyclic silazanes or silathianes are condensed with such activated carbonyl derivatives resulting in macrocyclic ureas, amides, and macrocyclic thiolactones, respectively.

The macrocyclic compounds prepared according to the process of the present invention, and novel macrocyclic compounds according to the invention have various uses. A large part of the novel compounds are effective complexing agents, especially of cations. Such macrocyclics can thereby serve as catalysts, as analytical agents and as key components for the separation of organic and inorganic ions. Due to these complexation properties, macrocycles may serve as valuable pharmaceutical agents, and especially antibiotically active substances.

BACKGROUND OF THE INVENTION

Macrocyclic compounds are receiving increasing attention due to their outstanding physical and chemical properties and their remarkable physiological activities.

Macrocyclic compounds may serve as fragrances or fragrance carriers. Amongst the most powerful representatives of this family may be mentioned muscone and muscone derivatives. Other macrocyclic compounds may be effective complexing agents for both organic and inorganic ions. As complexing agents they do serve as catalysts for organic synthesis, as separation agents for various cations or anions and as analytical tools for the identification of specific metal ions. In addition, some macrocyclic polyamides and lactones are also known to be effective antibiotics, while others show promising features as chemotherapeutic agents for the treatment of neoplastic diseases.

SUMMARY OF THE INVENTION

The novel method of the present invention provides easy and convenient access to a large variety of macrocyclic carbonyl compounds. The process is comparatively simple and is carried out under smooth reaction conditions, giving comparatively high yields. The novel process also provides a convenient route to the synthesis of known macrocyclic compounds.

According to a preferred embodiment of the invention cyclic stannoxanes are prepared from diols, such as alkyl diols, aryl diols, aralkyl diols, diols containing additional, non interfering functional groups such as ether groups, thioether groups, amino groups, carbonyl groups, ester groups, halide or nitrile groups, and tin oxide derivatives, such as dialkyl tin oxide, diaryl tin oxide or alkylaryl tin oxide, or from diols (as specified above) and tin dialkoxide derivatives such as dialkyl tin dialkoxide, diaryl tin dialkoxide or aralkyl tin dialkoxide, and such stannoxanes are reacted with an activated carbonyl derivative to yield macrocyclic carbamates or lactones.

Amongst suitable activated carbonyl derivatives there may be mentioned diisocyanates, diacyl chlorides, acyl anhydrides or $\beta$-lactones. According to a further embodiment of the invention, cyclic stannoxanes are condensed with optically active acidic amino acid derivatives resulting in chiral macrocyclic structures. According to yet a further embodiment of the invention cyclic silazanes or silathianes are condensed with such activated carbonyl derivatives resulting in macrocyclic ureas, amides and macrocyclic thiolactones, respectively.

The macrocyclic compounds prepared according to the process of the present invention, and novel macrocyclic compounds according to the invention have various uses. A large part of the novel compounds are effective complexing agents, especially of cations. Such macrocyclics are useful as catalysts, as analytical agents and as key components for the separation of organic and inorganic ions. Due to their complexation properties, macrocyclics of this type are valuable pharmaceutical agents, and especially antibiotically active substances.

The following reaction scheme illustrates the invention:

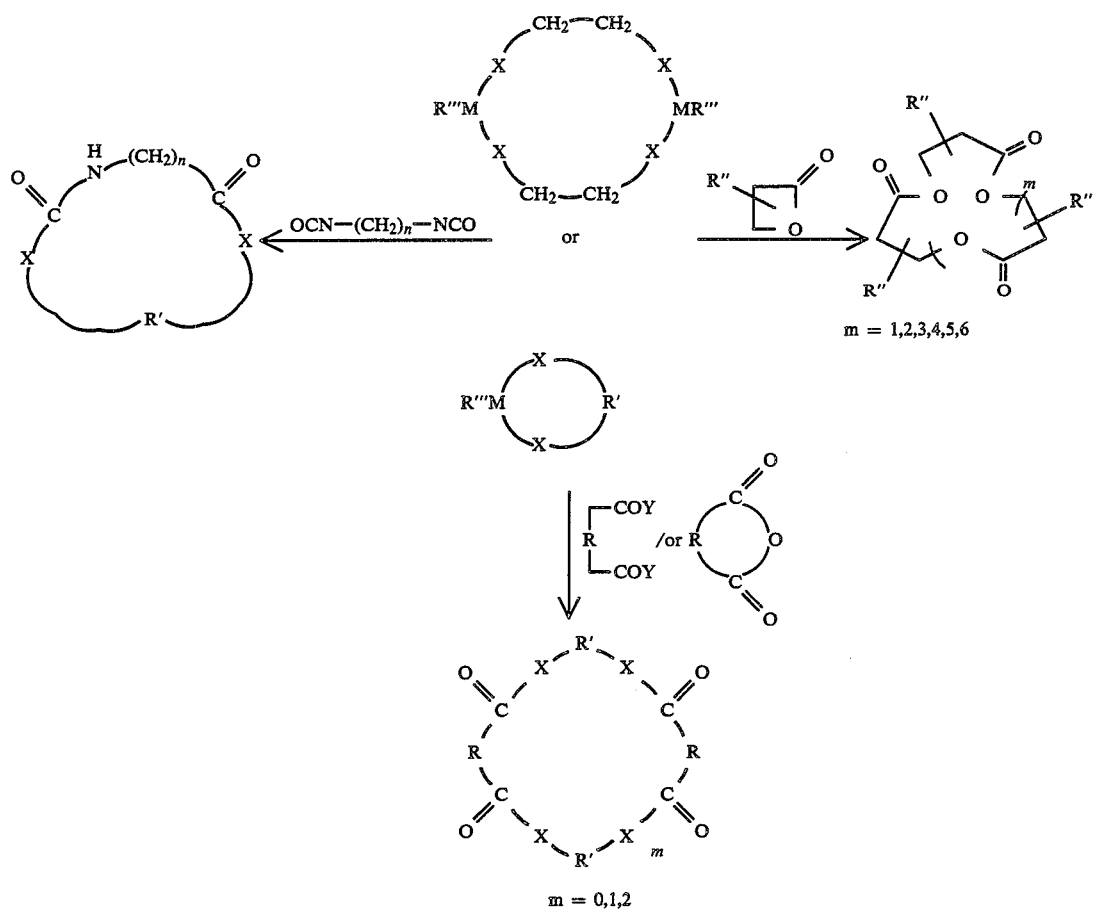

wherein
R, R', R" and R'" which may be identical or different, each designates alkyl or aryl, optionally containing —O—, —S—, NR, —CO—, —NRCO—, —COO— etc;
Y is a halogen or an imidazole, thioalkyl, thioaryl or any good leaving group;
X is NR, S, O;
n is an integer of from 1 to 12;
M is Si, Sn.

The synthesized macrocyclic compounds have been shown to effectively bind metal ions and to extract them from aqueous to organic solution.

Specifically, the polylactones 12 and 13 (example 7, scheme 13) have been found to bind rare earth metals ions such as europium. The binding capability of these systems was demonstrated by nmr measurements: addition of europium ions to a solution of either the lactone 12 or lactone 13 caused a downfield shift of the nmr signals, which is evidence for binding.

The macrocyclic thiolactones, were found to extract heavy metals such as mercury or silver from water into chloroform solution. The hexathiolactone 6 (Example 4, scheme 4a, n=3, m=2) was found to extract mercuric chloride quantitatively from an aqeous solution into chloroform, and the tetrathiolactone 6 (Example 4, scheme 4a, n=5, m=1) was found to extract silver acetate from water into chloroform.

The diureas were found to form channels in the solid state into which guest molecules may be incorporated (clathrate complexes).

DETAILED DESCRIPTION OF THE INVENTION

The invention is illustrated with reference to the following examples which are to be construed in a non-limiting manner.

EXAMPLE 1

Preparation of Dicarbamate (Scheme 1a, n=6)

A quantity of 2.36 g (4.0 mmol) distannoxane was dissolved in 30 ml carbon tetrachloride and there was added at room temperature dropwise a quantity of 1.29 ml (8 mmol) 1,6-diisocyanato hexane in 9 ml carbon tetrachloride. After completion of the addition, the reaction mixture was refluxed for 1 hour, 5 ml THF (5%) was added and the resulting precipitate of dibutyl tin oxide was filtered off. The filtrate was concentrated and the residue was crystallized from 1:1 benzene/petrol ether, resulting in 0.64 g (35% yield) of the desired carbamate (M.P. 168° C.)

EXAMPLE 2

Preparation of Tetralactone (Scheme 2a, n=8)

A quantity of 1.758 g (3.0 mmol) distannoxane was dissolved in 70 ml carbon tetrachloride under reflux, and there was added dropwise 1.434 g (6 mmol) sebacoyl chloride. The reaction mixture was refluxed during 20 hours and after this period of time concentrated to give a solid residue. Chromatography gave 0.413 mg (9.06.10$^{-4}$ mol) of pure tetralactone which was recrystallized from methylene chloride/pentane.

In a similar manner other tetralactones were prepared. The results are summarized in Table I.

EXAMPLE 3

Preparation of Macrocyclic Amino Acid Derivatives (Scheme 3a)

Stannoxane 1 (1.682 g, 2.88.10$^{-3}$ m) and 1.455 g (6.89.10$^{-3}$ m) aspartic acid anhydride 2a were dissolved in 150 ml boiling chloroform and heating continued under reflux for 1 hour. The mixture was then concentrated in vacuo and chromatographed on silica gel. Elution with benzene-ethyl acetate afforded 181 mg (3.73.10$^{-4}$ m, 13%) of 3a and 1.037 g (2.03.10$^{-3}$ m, 70.5%) of 4a. Compound 3a exhibited: M.P. 138°–140° C. (benzene-ethyl acetate); $[\alpha]_D = -31.5$ (c=0.475 in ethanol); i.r. (nujol) $\nu$3300, 1755, 1170. 910 and 890 cm$^{-1}$; nmr (DMSO)$\delta$ 2.730 (d of d, $J_{gem.}$=17 Hz, $j_{vic.}$=6.2 Hz, 2H, CH$_2$COOH), 2.88 (d of d, $J_{gem.}$=17 Hz, $J_{vic.}$=5.1 Hz, 2H, CH$_2$COOH), 3.62 (s, 4H, OCH$_2$CH$_2$O), 4.701 (d of d, $J_{vic.}$=8.6 Hz, $J_{vic.}$=5 Hz, 2H, CH—CH$_2$COOH) and 9.87 ppm (d, $J_{vic.}$=9 Hz, 2H, NH). Mass spectrum, highest fragment, m/e=466 (C$_{14}$H$_{14}$F$_6$N$_2$O$_{10}$—H$_2$O). Compound 4a exhibited: $\alpha_D = -50.6$ (c=1.73 in ethanol); ir (nujol) $\nu$3300, 1720, 1550, 1280, 1220, 1180, 1075 and 900 cm$^{-1}$; $^1$H nmr (CD$_3$OD) $\delta$ 2.46 (d of d, $J_{gem.}$=17 Hz, $J_{vic.}$=8.0 Hz, 1H, CH$_2$CO), 2.58 (d of d, $J_{gem.}$=17 Hz, $J_{vic.}$=5.0 Hz, 1H, CH$_2$CO), 3.32 (d of d, $J_{vic.}$=4.5 and 5.4 Hz, 2H, CH$_2$O), 3.8 (d of d, $J_{vic.}$=4.5 and 5.4 Hz, 2H, C$^2$H$_2$O), and 4.48 ppm (m, 1H, CH NH); $^{13}$C nmr (CD$_3$OD) $\delta$ 172.95 (s, CH$_2$CO), 170.20 (s, CHCO), 158.40 (q, J=40 Hz, COCF$_3$), 116.75 (q, J=286.5 Hz, CF$_3$), 67.75 (t, J=68 Hz, C$^2$H$_2$O), 60.25 (t, J=49.6, C$^1$H$_2$O), 50.25 (d, J=78.0 Hz, CHNH) and 35.5 ppm (m, CH$_2$CO); mass spectrum, molecular peak m/e=510 (C$_{16}$H$_{16}$F$_3$N$_2$O$_{10}$).

Application of the same procedure to D-trifluoroacetyl aspartic acid anhydride (2b) afforded the corresponding enantiomers 3b, [M.P. 140° C.; $[\alpha]_D = +30.7$ (c=0.45 in ethanol)], and 4b [M.P. 76°–78° C., $[\alpha]_D = +46.1$ (c=0.475 in ethanol)].

EXAMPLE 4

Preparation of Macrocyclic Tetrathiolactones (Scheme 4a, n=8, m=1)

A solution of 0.9 ml (6.65.10$^{-3}$ m) 2,2-dimethyl-2-sila-1,3-dithiocylopentane 5 in 20 ml tetrahydrofuran was treated with a solution of 1.31 ml (6.65.10$^{-3}$ m) sebacoyl chloride in 5 ml tetrahydrofuran. The reaction mixture was subsequently heated under reflux for 2.5 hours and the mixture concentrated in vacuo. Crystallization of the residue from either toluene or tetrahydrofuran and subsequent chromatography on silica gel afforded the analytically pure tetrathiolactone 6. The structure of the product was identified by its analytical and spectropscopic properties. Compound 6 exhibited: M.P. 121°–124° C.; ir (KBr) $\nu$2920, 2845, 1685, 1470, 1400, 1350, 1200, 1140, 1060, 965, 760 and 715 cm$^{-1}$; nmr (CDCl$_3$)$\delta$ 3.07 (s, 8H, CH$_2$—S), 2.55 (t, J=7 Hz, 8H, CH$_2$—CO), 1.64 (m, 8H, CH$_2$CH$_2$CO) and 1.29 ppm (broad s, 16H, —CH$_2$CH$_2$CH$_2$); mass spectrum, molecular ion m/e=520, base peak m/e=200. Elemental analysis: found: C 55.20, H 7.79, S 23.50%; calculated for C$_{24}$H$_{40}$O$_4$S$_4$: C 55.37, H 7.75, S 24.62%.

Following the same reaction procedure macrocyclic ethylene azelate, pimelate and glutarate have been prepared in 14, 9 and 11% chemical yield respectively without optimizing reaction conditions. All compounds have been characterized by their analytic and spectropscopic properties which were in agreement with the assigned structures. No evidence for the formation of the corresponding cyclic dithiolactones has been found in any of the case studies. The properties of the macrocyclic thiolactones are summarized in Table I.

EXAMPLE 5

Preparation of Diurea (Scheme 5, n=6)

A solution of 1.6257 g (9.45.10$^{-3}$ m) cyclic silazane 7 in 15 ml dichloroethane and 1.514 ml (9.45.10$^{-3}$ m) 1,6-diisocyanato hexene were added simultaneously and dropwise to 70 ml dichloroethane at room temperature. After completion of the addition the reaction mixture was heated to reflux for 5 hours and subsequently treated with 10 ml of 95% aqueous ethanol for one hour at the same temperature. The resulting precipitate was filtered to give 483 mg (18%) of the diurea 8 (M.P. 271°–274° C.).

EXAMPLE 6

Preparation of Tetralactone (Scheme 6a)

A solution of 1.48.10$^{-2}$ m cyclic stannoxane 9 in 100 ml dry chloroform was treated dropwise under reflux with a solution of 2.33 ml (1.48.10$^{-2}$ m) pimeloyl chloride in 100 ml dry chloroform. Reflux was continued for 2 hours, the reaction mixture concentrated in vacuo and the residue chromatographed on silica gel to give 1.64 g (3.59.10$^{-3}$ m, 48.6%) of the tetralactone 10 (M.P. 90°–95° C.).

EXAMPLE 7

Preparation of Tri-, Tetra-, and Pentalactones 11, 12, 13 (Scheme 7a)

A solution of 5.9 g stannoxane 1, 5.9 g (10$^{-2}$ m) in 400 ml dry chloroform is treated under reflux for 4 hours with 2.46 (4.10$^{-2}$ m) propiolactone. Concentration of the reaction mixture in vacuo and chromatography through silica gel gave 694 mg (24%) of the trimer 11 (M.P. 56°–58° C.), 386 mg (13%) of the tetramer 12 (M.P. 116°–120° C.), and 260 mg (9%) of the pentamer 13 (M.P. 80°–85° C.)

EXAMPLE 8

Extraction of Heavy Metal Ions from Aqeous Solutions into Organic Solvents with Macrocyclic Thiolactones 8a: Extraction of mercury chloride from water by thiolactone 6 (Example 4, scheme 4a, n=3, m=2)

An amount of 30 mg thiolactone 6 was dissolved in 10 ml chloroform, and an amount of 20 ppm mercury chloride in 40 ml water. The organic solution was then shaken with the aqeous solution. After 10 minutes of treatment, more than 90% of the mercury salt has been found to have been extracted into the organic phase, after 1 hour of treatment, less than 100 ppb has been found to have remained in the water.

8b: Extraction of silver acetate from water by thiolactone 6 (Example 4, scheme 4a, n=5, m=1)

A 10$^{-4}$M solution of thiolactone in chloroform was shaken with an equal volume of a 10$^{-6}$M solution of silver acetate in water for 1 hour. Then the phases were separated and the aqeous phase analyzed for silver ions.

10% of the salt has been found to have been removed from the water solution.

TABLE I

| n | M.P. | mass spectrum | molecular formula |
|---|---|---|---|
| MACROCYCLIC TETRALACTONES | | | |
| 2 | 90° C. | 288 | $C_{12}H_{16}O_8$ |
| 3 | 144° C. | 316 | $C_{14}H_{20}O_8$ |
| 4 | 56° C. | 344 | $C_{16}H_{24}O_8$ |
| 5 | 147° C. | 372.44 | $C_{18}H_{28}O_8$ |
| 6 | 54° C. | 400 | $C_{20}H_{32}O_8$ |
| 7 | 147° C. | 428.521 | $C_{22}H_{36}O_8$ |
| 8 | 79° C. | 456.576 | $C_{24}H_{40}O_8$ |
| 3 + 4 | 70° C. | 330 | $C_{15}H_{22}O_8$ |
| 6 + 7 | 122° C. | 414 | $C_{21}H_{34}O_8$ |
| MACROCYCLIC TETRATHIOLACTONES | | | |
| 3 | 140–145° C. | 380 | $C_{14}H_{20}S_4O_4$ |
| 5 | 125–129° C. | 436 | $C_{18}H_{28}S_4O_4$ |
| 7 | 70° C. | 492 | $C_{22}H_{36}S_4O_4$ |
| 8 | 121° C. | 520 | $C_{24}H_{40}S_4O_4$ |

We claim:

1. A process for the production of macrocyclic carbonyl compounds having 2–8 carbonyl groups and at least 4 carbonyl groups when the ring contains only oxygen hetero-atoms which comprises reacting a cyclic metolloid silazane compound and an isocyanate in an organic solvent to form a diurea derivative, said cyclic metalloid being devoid of functional groups apt to interact with the activated carbonyl derivative.

2. A process for the production of macrocyclic carbonyl compounds having 2–8 carbonyl groups and at least 4 carbonyl groups when the ring contains only oxygen hetero-atoms which comprises reacting a cyclic metolloid silazane compound with an acyl chloride in an organic solvent to form a polyamide, said cyclic metolloid being devoid of functional groups apt to interact with the activated carbonyl derivative.

3. A process for producing a product of the formula

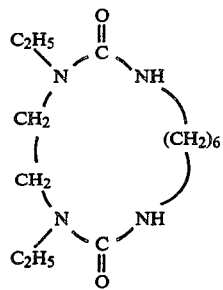

which comprises reacting 1,3-diethyl-2,2-dimethyl-1,1,3-diaza-2-silacyclopentane and 1,6-diisocyanato hexane in an organic solvent.

4. A process for the production of macrocylclic carbonyl compounds having at least 4 carbonyl groups of the formula

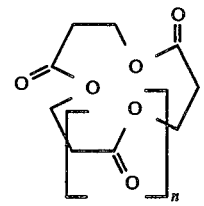

wherein N is 1, 2, or 3 comprosing reacting a cyclic metalloid stannoxane derivative with propiolactone in an organic solvent, said cyclic metalloid derivative being devoid of functional groups apt to interact with the activated carbonyl derivatives.

5. A compound of the formula

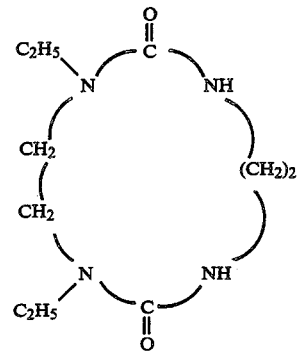

6. A compound of the formula

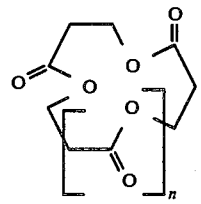

wherein n = 1, 2, 3, 4, 5 or 6.